United States Patent [19]

Marfat

[11] Patent Number: 4,761,485

[45] Date of Patent: Aug. 2, 1988

[54] SYNTHETIC METHOD FOR INDOL-2(3H)-ONES

[75] Inventor: Anthony Marfat, Mystic, Conn.

[73] Assignee: Pfizer Inc., New York, N.Y.

[21] Appl. No.: 24,746

[22] Filed: Mar. 11, 1987

[51] Int. Cl.$^4$ ..................... A61K 31/40; C07D 209/34
[52] U.S. Cl. .................................... 548/486; 260/694; 548/490
[58] Field of Search ............................... 548/486, 490

[56] References Cited

U.S. PATENT DOCUMENTS

| | | | |
|---|---|---|---|
| 2,335,273 | 11/1943 | Haller | 548/486 |
| 4,105,663 | 8/1978 | Bagli | 544/379 |
| 4,480,118 | 10/1984 | Tsushima | 260/544 D |
| 4,556,672 | 12/1985 | Kadin | 514/414 |
| 4,727,073 | 2/1988 | Takaya | 514/252 |

OTHER PUBLICATIONS

Parrick et al., Tetrahedron Letters, vol. 25, pp. 3099–3100, (1984).
Sumpter et al., J. Am. Chem. Soc., vol. 67, pp. 1656–1658, (1945).
Michaelis, Chem. Ber., vol. 30, pp. 2809–2821, (1897).
Beckett et al., Tetrahedron, vol. 24, pp. 6093–6109, (1968).
Sumpter et al., "The Chemistry of Heterocyclic Compounds", vol. 8, Weissberger, ed., Interscience Publishers, 1954, pp. 134–138.
Livingston in "Rodd's Chemistry of Carbon Compounds", vol. IV, part A, 2nd ed., Coffey, ed., Elsevier, 1973, pp. 448–451.
Livingstone in "Supplements to the 2nd ed. of Rodd's Chemistry of Carbon Compounds", vol. IV, part A, Ansell, ed., Elsevier, 1984, pp. 440–441.
DaSettimo et al., J. Org. Chem., vol. 39, pp. 1995–1998, (1974).

*Primary Examiner*—Donald G. Daus
*Assistant Examiner*—Mark W. Noel
*Attorney, Agent, or Firm*—Peter C. Richardson; Albert E. Frost; Robert K. Blackwood

[57] ABSTRACT

A two-step process for the synthesis of certain indol-2(3H)-ones from indoles, and the 3,3-dibromoindol-2(3H)-ones which are intermediates in that process.

2 Claims, No Drawings

SYNTHETIC METHOD FOR INDOL-2(3H)-ONES

BACKGROUND OF THE INVENTION

The present invention is directed to a two-step process for certain indol-2(3H)-ones (otherwise known as oxindoles, 2-oxindoles, 2-oxoindolines, or in their tautomeric form, as 2-hydroxyindoles), and to the intermediate 3,3-dibromoindol-2(3H)-ones employed in that process. Those of the present indol-2(3H)-ones which are monosubstituted on the benzene ring with $C_1$-$C_3$)alkyl, $C_1$-$C_3$)alkoxy or halogen are reported to have utility in the treatment of anxiety and tension (Molloy, U.S. Pat. No. 3,882,236). More particularly, all of the presently synthesized indol-2(3H)-ones are useful as intermediates in the synthesis of the analgesic/antiinflammatory 3-substituted 2-oxindole-1-carboxamides of Kadin, U.S. Pat. No. 4,556,672. Throughout the present text the products of the present invention are alternatively named as indol-2(3H)-ones (the more systematic name, based on Rigaudy et al. "IUPAC Nomenclature of Organic Chemistry", Pergammon Press, 1979, pp. 58, 172–173) and as oxindoles (a name finding common use in the literature).

Prior syntheses of present oxindoles have been reviewed, for example, by Sumpter et al., "The Chemistry of Heterocyclic Compounds", vol. 8, Weissberger, ed., Interscience Publishers, Inc., 1954, pp 134–138; and by Livingstone, in "Rodd's Chemistry of Carbon Compounds" 2nd. Edition, vol. 4, part A, S. Coffey, ed., Elsevier Scientific Publishing Co., 1973, pp. 448–451 and in "Supplements to the 2nd Edition of Rodd's Chemistry of Carbon Compounds", vol. 4, part A, M. F. Ansell, ed., Elsevier, 1984, pp. 440–441. For the most part by far, the synthetic methods for said oxindoles reflect cyclization of suitably substituted benzene derivatives. However, Beckett et al., Tetrahedron, vol. 24, pp. 6093–6109 (1968) prepared indol-2(3H)-one itself by the hydrogenation of an acidic ethanol solution of isatin over 10% Pd/C catalyst. Michaelis, Chem. Ber., vol. 30, pp. 2809–2821 (1897) and Coleman, Ann., vol. 248, pp. 114–120 (1888) converted N-alkylindoles to N-alkyloxindoles via 3,3-dibromo-N-alkyloxindoles, using sodium hypobromite for the first step and zinc/HCl reduction for the second.

Some of the present class of 3,3-dibromoindol-2(3H)-ones are known in the literature, but are of no specified utility. These are 3,3-dibromoindol-2(3H)-one itself and corresponding 5-bromo, 5,6-dibromo, 5,7-dibromo and 4,7-dimethoxy analogs; Sumpter et al., J. Am. Chem. Soc., vol. 67, pp. 1656–1657 (1945); DaSettimo, J. Org. Chem., vol. 39, pp. 1995–1998 (1974); and Parrick et al., Tetrahedron Lett., vol. 25, pp. 3099–3100 (1984). The earliest reference obtained these 3,3-dibromo compounds from the desired oxindole; the intermediate one by bromination of 2,3-dibromoindoles; and the latest by the action of N-bromosuccinimide (not pyridinium perbromide) on indoles or 3-bromoindoles.

SUMMARY OF THE INVENTION

The present invention is directed to a process for the preparation of an oxindole of the formula

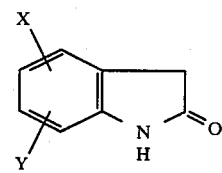

wherein X and Y are each independently hydrogen, $(C_1$-$C_3)$alkyl, $(C_1$-$C_3)$alkoxy, fluoro, chloro or bromo, which comprises the sequential steps of
(a) reacting an indole of the formula

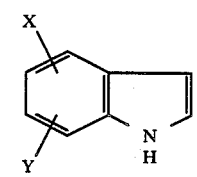

with substantially 3 molar equivalents of pyridinium bromide perbromide in a reaction-inert solvent to yield an intermediate dibromooxindole of the formula

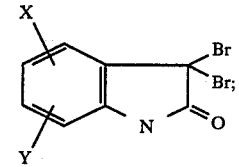

and either
(b₁) hydrogenating said dibromooxindole over a noble metal catalyst in a reaction-inert solvent to yield said oxindole of the formula (I); or
(b₂) debrominating said dibromooxindole with zinc dust in a lower aliphatic carboxylic acid to yield said oxindole of the formula (I).

As used above and elsewhere herein, the expression "reaction-inert solvent" refers to a solvent which does not significantly reduce the yield of the desired product by interaction with the starting materials, reagents, intermediates or products. The expression "lower aliphatic carboxylic acid" refers to a straight or branched chain ($C_2$-$C_6$) alkanoic acid.

When step (b₁) is employed, the preferred noble metal catalyst is palladium, more preferably palladium supported on carbon, most preferably using ethanol as solvent. When step (b₂) is employed, the preferred carboxylic acid is acetic acid. In any case, the preferred solvent in step (a) is t-butanol.

It is particularly advantageous to carry out the present process on commercially available 5-chlorindole, producing 5-chloroindol-2(3H)-one, an intermediate for Kadin's particularly valuable 5-chloro-3-(2-thenoyl)-2-oxindole-1-carboxamide (Kadin, loc. cit.).

The present invention is also directed to the intermediate compounds of the formula (III), excluding the prior known compounds of this class which are listed above.

DETAILED DESCRIPTION OF THE INVENTION

The present invention is readily carried out. In the first step, the indole of the formula (II) is treated with substantially 3 molar equivalents of pyridinium bromide perbromide in a reaction inert solvent. t-Butanol is the preferred solvent for this purpose. The temperature is not critical. For example, temperatures in the range of 0°–50° C. are generally satisfactory. Ambient temperatures, e.g., 17°–30° C. avoiding the cost of external heating or cooling, are most convenient. The resulting 3,3-dibromo intermediate, of the formula III, is isolated by standard methods of solvent evaporation, extraction, crystallization and chromatography.

The second step didebromination to form the indol-2(3H)-one (oxindole) of the formula (I) is optionally carried out by hydrogenation over a noble metal catalyst in a reaction-inert solvent. The noble metal catalysts employed in the present invention include platinum, palladium, rhodium and ruthenium, either of the supported or non-supported type, as well as the known catalytic compounds thereof such as the oxides, chlorides, etc. Examples of suitable catalyst supports include carbon, silica, calcium carbonate and barium sulfate. The catalysts may be performed or formed in situ by prereduction of an appropriate salt of the catalytic compound. The preferred noble metal in the present case is palladium. Most preferred is 5–10% palladium supported on carbon. The temperature of the present hydrogenation is not critical, temperatures in the range 0°–60° C. being generally satisfactory. Ambient temperatures, for the reasons stated above in the halogenation step, are most convenient. Likewise, hydrogenation pressure is not critical, pressures in the range of 1–100 atmospheres being generally satisfactory. However, to avoid the undue expense of high pressure equipment, pressures in the range of 1 to about 10 atmospheres are preferred. Once hydrogenolysis of the 3,3-dibromo groups is complete, the valuable catalyst is generally recovered by filtration and recycled in the hydrogenation if still active, or reprocessed to recover to the noble metal and/or convert it to fresh catalyst. The desired oxindole is then recovered from catalyst mother liquors and purified by standard methods of concentration, extraction and crystallization.

Alternatively, the second step didebromination to form the indol-2(3H)-one of the formula (I) is carried out by the action of zinc in a lower aliphatic carboxylic acid, preferably acetic acid. Again, temperature is not critical, temperatures in the range 0°–50° C. being generally satisfactory, and ambient temperatures most convenient and least costly.

Many of the indoles required for the present synthesis of indol-2(3H)-ones are available commercially. For example, indole, 5-bromoindole, 4-, 5- and 6-chloroindoles, 5-fluoroindole, 4-, 5-, 6- and 7-methylindoles, 4- and 5-methoxyindoles and 5,6-dimethoxyindole are available from Aldrich Chemical Co., Inc., 940 West Saint Paul Avenue, Milwaukee, Wis. 53233, U.S.A. Those for which a commercial source is not identified are available by one or more of an estensive number of literature methods, as summarized, for example in "Rodd's Chemistry of Carbon Compounds", 2nd Edition, S. Coffey, editor, Volume IVA, Elsevier Scientific Publishing Co., 1973, pp. 397–405; Sundberg, "Comprehensive Heterocyclic Chemistry", vol. 4, Katritzky et al., eds., Pergammon Press, 1984, pp. 313–369; and Sumpter et al., "The Chemistry of Heterocyclic Compounds", vol. 8, Weissberger, ed., Interscience Publishers, Inc., 1954, pp. 3–23.

The present invention is illustrated by the following examples, but not limited to the specific details thereof.

EXAMPLE 1

3,3-Dibromo-5-chloroindol-2(3H)-one

To a solution of 5-chloroindole (1.00 g) in t-butanol (65 ml) was added portionwise over 0.5 hr 6.9 g of pyridinium bromide perbromide. The reaction mixture was stirred at room temperature for 2 hours after which TLC analysis (1:1 ethyl acetate/hexane) indicated complete conversion of starting material to several products. The reaction mixture was diluted with ethyl acetate (400 ml) and $H_2O$ (400 ml). The organic layer was separated and the aqueous layer extracted with ethyl acetate (300 ml). The combined organic extracts were washed with $H_2O$ (2×400 ml) and brine, dried ($Na_2SO_4$) and concentrated in vacuo to a yellow-green oil. Purification on a silica gel column eluted with 40% ethyl acetate/hexane afforded the more polar product (3,3-dibromo-5-chlorooxindole) as a brown solid (1.26 g, 60%).

In like manner, indole and 4-, 5- and 6-chloro-, 5-fluoro, 4-, 5-, 6- and 7-methyl, 4- and 5-methoxy-and 5,6-dimethoxy-indoles are converted to indole-2(3H)-one and corresponding substituted indol-2(3H)-ones, respectively.

EXAMPLE 2

5-Chloroindol-2(3H)-one (5-Chloro-2-Oxinole)

Method A

A mixture of title product of the preceding Example (1.28 g) in absolute ethanol (100 ml) was hydrogenated at 5 psi in the presence of 10% palladium on carbon (800 mg). After 20 minutes TLC analysis (10% ethyl acetate/$CH_2Cl_2$) indicated complete conversion of starting material to a single more polar product. The reaction mixture was filtered over diatomaceous earth, the filter cake washed with ethanol and then methanol, and the filtrate concentrated in vacuo to a tan solid (870 mg). Purification on a silica gel column eluted with 5% $CH_3OH/CH_2Cl_2$ afforded 520 mg (79%) of title product, mp=196°–198° C. (lit. mp=195°–196° C.; Can. J. Chem. vol. 41, 2399, 1963).

Method B

To a solution of title product of the preceding Example (1.5 g) in glacial acetic acid (40 ml) was added 3.02 g (10 equiv.) of zinc dust (325 mesh). The reaction mixture, which turned slightly exothermic, was stirred at room temperature. TLC analysis (5% $CH_3OH/CH_2Cl_2$) after 0.5 hr indicated complete conversion of starting material to the more polar product. The reaction mixture was filtered, washed well with ethyl acetate, and the filtrate concentrated in vacuo to a light tan semisolid. This was redissolved in ethyl acetate (200 ml), washed with $H_2O$ (2x) and brine (1x), dried over $Na_2SO_4$, and concentrated in vacuo to give 0.77 g of light tan crystalline product.

Recrystallization from 30 ml ethanol afforded 0.57 g of purified title product, mp=196°–198° C., identical to the product of Method A.

By the same alternative methods, the other products of the preceding Example are converted to indol-2(3H)-one and corresponding indol-2(3H)-ones substituted on the aromatic ring.

I claim:
1. A compound of the formula

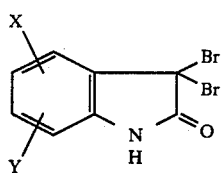
wherein X and Y are each independently hydrogen, $(C_1-C_3)$alkyl, $(C_1-C_3)$alkoxy, fluoro, chloro or bromo; with the provisos that both X and Y are not hydrogen; when X or Y is 5-bromo, the other is not hydrogen, 6-bromo or 7-bromo; and when X or Y is 4-methoxy, the other is not 7-methoxy.
2. The compound of claim 1 wherein X is 5-chloro and Y is hydrogen.
* * * * *